(12) United States Patent
Gaspredes et al.

(10) Patent No.: US 10,806,506 B2
(45) Date of Patent: Oct. 20, 2020

(54) VESSEL SEALING ALGORITHM AND MODES

(71) Applicant: Smith & Nephew, Inc., Memphis, TN (US)

(72) Inventors: Jonathan L. Gaspredes, Austin, TX (US); Robert P. Lathrop, Austin, TX (US); Thomas P. Ryan, Austin, TX (US); David J. Miller, Austin, TX (US); Jean Woloszko, Austin, TX (US); Philip M. Tetzlaff, Austin, TX (US)

(73) Assignee: Smith & Nephew, Inc., Austin, TX (US)

( * ) Notice: Subject to any disclaimer, the term of this patent is extended or adjusted under 35 U.S.C. 154(b) by 911 days.

(21) Appl. No.: 15/133,854

(22) Filed: Apr. 20, 2016

(65) Prior Publication Data

US 2016/0310203 A1 Oct. 27, 2016

Related U.S. Application Data

(60) Provisional application No. 62/150,512, filed on Apr. 21, 2015.

(51) Int. Cl.
*A61B 18/00* (2006.01)
*A61B 18/14* (2006.01)
*A61B 18/12* (2006.01)

(52) U.S. Cl.
CPC .. *A61B 18/1445* (2013.01); *A61B 2018/0063* (2013.01); *A61B 2018/0072* (2013.01);
(Continued)

(58) Field of Classification Search
CPC . A61B 18/1206; A61B 18/1445; A61B 18/18; A61B 2018/0063; A61B 2018/00755; A61B 2018/00875; A61B 2018/0072; A61B 2018/00726; A61B 2018/00958; A61B 2018/126;
(Continued)

(56) References Cited

U.S. PATENT DOCUMENTS

| 2002/0032439 A1* | 3/2002 | Hareyama | A61B 18/1206 606/38 |
| 2009/0157072 A1* | 6/2009 | Wham | A61B 18/1206 606/33 |
| 2011/0144635 A1* | 6/2011 | Harper | A61B 18/1206 606/34 |

* cited by examiner

*Primary Examiner* — Jaymi E Della
*Assistant Examiner* — Rachel A. Vierra
(74) *Attorney, Agent, or Firm* — Norman F. Hainer, Jr.

(57) ABSTRACT

A method comprising sealing a vessel residing within tissue between jaws of forceps by sensing an amount of tissue held within the forceps, the sensing by passing electrical current through the tissue by way of the forceps. The method comprises heating the tissue using electrical current, the heating such that impedance of the tissue changes at a first predetermined rate, the first predetermined rate selected based on the sensing. The method comprises desiccating the tissue using electrical current, such that the impedance of the tissue changes at a second predetermined rate different than the first predetermined rate. The method comprises ceasing application of the electrical current to the tissue when impedance of the tissue reaches a predetermined value. Sensing the amount of tissue held within the forceps comprises varying electrical current flowing through the tissue through the forceps such that impedance of the tissue changes at a third predetermined rate.

24 Claims, 11 Drawing Sheets

(52) U.S. Cl.
CPC ............... *A61B 2018/00726* (2013.01); *A61B 2018/00875* (2013.01); *A61B 2018/00958* (2013.01); *A61B 2018/126* (2013.01)

(58) Field of Classification Search
CPC ........... A61B 2018/00648; A61B 2018/00636; A61B 2018/00642; A61B 2018/00684; A61B 2018/00666; A61B 2018/00696; A61B 2018/00702; A61B 2018/00767; A61B 2018/00773; A61B 2018/00779; A61B 2018/00892
See application file for complete search history.

VESSEL SEALING ALGORITHM AND MODES

CROSS REFERENCE TO RELATED APPLICATIONS

This application claims the benefit of provisional application Ser. No. 62/150,512 filed Apr. 21, 2015, titled "Vessel Sealing Algorithm and Modes," which provisional application is incorporated by reference herein as if reproduced in full below.

BACKGROUND

Electrosurgical systems are used by physicians to perform specific functions during surgical procedures. Particular systems may be used to perform surgical procedures including sealing vessels residing within tissue. Any advances that increase the amount of control a surgical instrument provides during surgical procedures would result in a competitive advantage.

BRIEF DESCRIPTION OF THE DRAWINGS

For a detailed description of exemplary embodiments, reference will now be made to the accompanying drawings in which.

DEFINITIONS

Figure 1:
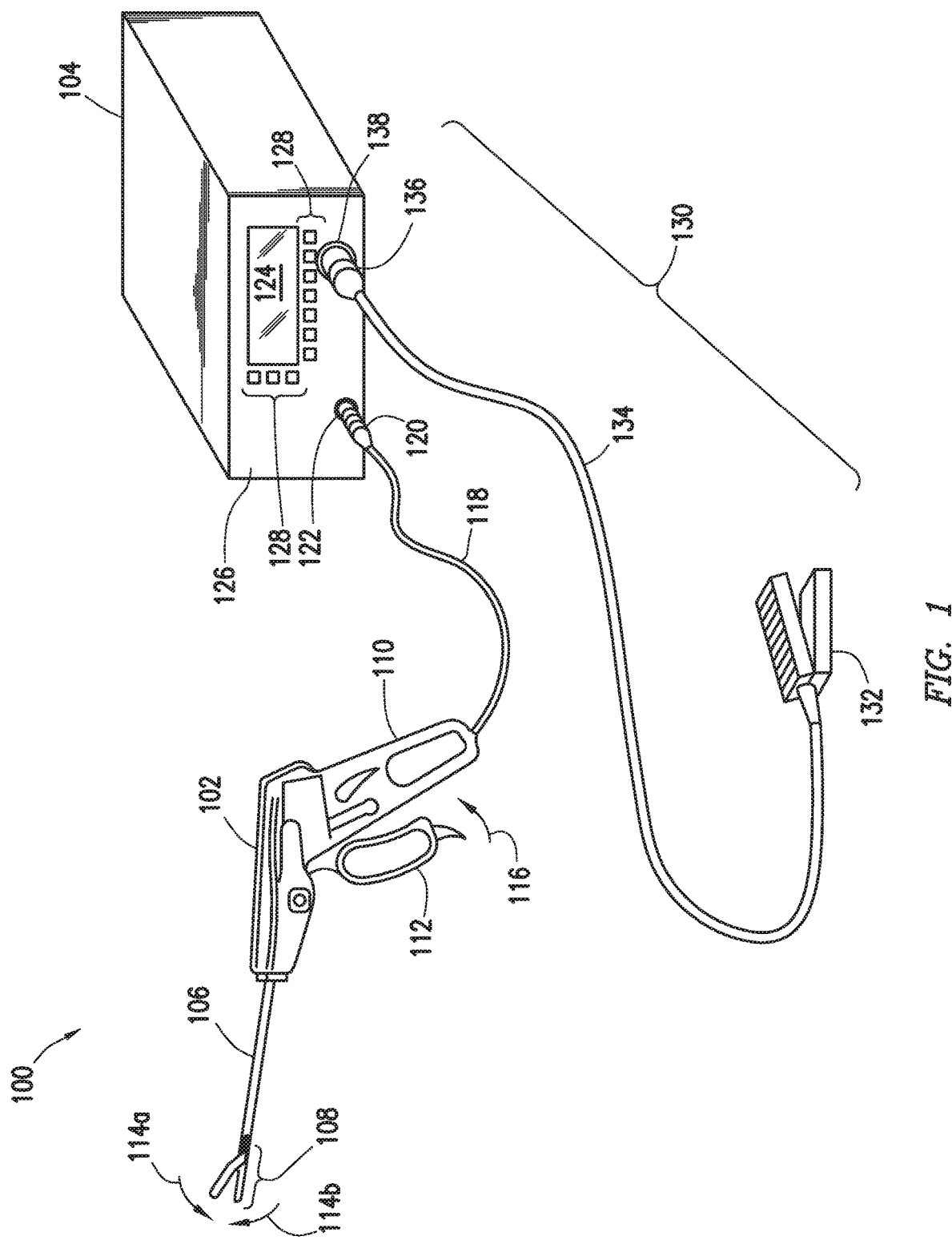
FIG. 1 shows a vessel sealing system in accordance with at least some embodiments.

Certain terms are used throughout the following description and claims to refer to particular system components. As one skilled in the art will appreciate, different companies may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

Reference to a singular item includes the possibility that there are plural of the same items present. More specifically, as used herein and in the appended claims, the singular forms "a," "an," "said," and "the" include plural references unless the context clearly dictates otherwise.

Various units, circuit, or other components in this disclosure may be described or claimed as "configured to" perform a task or tasks. In such contexts, "configured to" is used to connote structure by indicating that the units/circuits/components include structure (e.g., circuitry) that performs those tasks or tasks during operation. As such, the unit/circuit/component can be said to be configured to perform the task even when the specified unit/circuit/component is not currently operational (e.g., is not on). The units/circuits/components used with the "configured to" language include hardware—for example, circuits, memory storing program instructions executable to implement the operation, etc. Reciting that a unit/circuit/component is "configured to" perform one or more tasks is expressly intended not to invoke 35 U.S.C. § 112(f) for that unit/circuit/component.

"Heating" with respect to tissue shall mean increasing temperature of tissue toward or beyond the boiling point of moisture in the tissue, the increasing temperature by way of conduction of electrical current through at least some of the tissue. The fact that other portions of the tissue may be heated by convective heat transfer from areas where conduction takes place shall not obviate the status of "heating." Moreover, the fact that some desiccation may take place during heating shall not obviate that heating is taking place regarding the tissue as a whole.

"Desiccation" with respect to tissue shall mean driving off moisture by continuing to add energy to the moisture while the moisture is at boiling point. The fact that small pockets of moisture within the tissue may also be heated to the boiling point (e.g., at the beginning of a desiccation phase) shall not obviate that desiccation is taking place regarding the tissue as a whole.

"About" in relation to a stated value shall mean the stated value plus or minus 10% (inclusive) of the stated value.

"Seal" or "sealing" with respect to a vessel or group of vessels shall mean a restructuring of the vessel walls in a seal area such that the vessel walls of a vessel are fused together as to become one structure with no visible lumen and flow through the vessel or group of vessels is blocked. Radio frequency (RF) coagulation, that generally shrinks the vessel wall tissue to reduce the vessel lumen in size while leaving the lumen intact, and may also coagulate blood within and around the vessel to occlude or plug the vessel shall not be considered "sealing" for purposes of the specification and claims.

"Vessel" shall include any single or bundle of arteries, a single or bundle of veins, or a bundle of both at least one artery and at least one vein. Additionally, "vessel" may include lymph nodes and ducts. All of the aforementioned vessels may be isolated or skeletonized or may alternatively also be in the form of un-skeletonized tissue bundles including both the vessel(s) as previously defined, at least partially surrounded and associated with fatty or connective tissue.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure is limited to that embodiment.

It is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

The various embodiments are directed to vessel sealing methods and related vessel sealing systems. In particular, the various embodiments are directed to a vessel sealing system having multiple modes that are configured for various aspects of sealing, such as speed of creating the seal and quality or strength of the seal. For example, one mode of operation may reduce the time taken to seal tissue and underlying vessels within the tissue. Another mode may increase a quality of seal resulting from the procedure but use more time to complete the seal. The multiple modes of operation are implemented by the surgical device and controller.

In various embodiments, a quality of seal may be defined by a reliability of a seal. For example, a better quality seal may comprise attributes such as an increased mechanical stability of the seal (increased burst pressure, more force used to peel the walls apart, etc.). In other examples, a quality of seal may be correlated with a seal length, where the seal length extends axially into a vessel. A greater seal length may correlate with an increased quality of seal.

The controller may enable the surgical device to tune an amount of electrical energy applied to targeted tissue containing one or more vessels based on a sensed amount of tissue present within the forceps. During one or more phases of a seal cycle, by way of varying an amount of electrical energy applied to targeted tissue, a controller may be configured to control a value of impedance of targeted tissue. That is, the controller may be configured to apply an amount of electrical energy to the targeted tissue such that an impedance of the tissue changes at one or more predetermined rates. It is noted, that although embodiments may describe the use of electrical current to control a value of impedance, these embodiments are not limited to the use of electrical current but rather a value of impedance may be controlled by way of methods implementing voltage control, power control, current control or any combination of the three. It follows, that as a value of impedance is controlled over time, a rate of change of impedance is also controlled. References to controlling a rate of change of impedance also refers to the underlying phenomenon of controlling a value of impedance of the tissue over time.

During a seal cycle, the ability to control a value of impedance over time of targeted tissue, enables a physician to treat targeted tissue more efficiently, reliably and evenly. The ability to treat targeted tissue more efficiently, reliably and evenly is made partially possible by the ability to control an amount of electrical current applied to the tissue based on a state of the tissue. In contrast, a controller that does not have a similar capability in adapting an amount of electrical current applied to targeted tissue based on a state of the targeted tissue lacks the ability to treat targeted tissue in a comparable manner. The specification first turns to an illustrative system to orient the reader.

FIG. 1 illustrates a vessel sealing system 100 in accordance with at least some embodiments. In particular, the vessel sealing system 100 comprises an exemplary surgical device 102 comprising forceps 106. The forceps 106 comprise an elongated shaft that defines a distal end comprising jaws 108. In various embodiments, jaws 108 may be placed around tissue so as to grasp and apply a predefined pressure to the tissue. Jaws 108 may also comprise electrodes electrically coupled to an energy based source (i.e., controller 104), configured to supply energy to the tissue placed between the jaws 108 in a bipolar fashion and treat the tissue.

The surgical device 102 further defines a handle 110 where a physician grips the surgical device 102 during surgical procedures. The handle 110 comprises an actuator 112 which a physician may translate in a direction 116 to move jaws 108 in respective directions 114a and 114b and apply a pre-determined grasping and compressing pressure on the targeted tissue between jaws 108. That is, a physician may squeeze the actuator 112 closer to the handle 110 to close the jaws 108 and release the actuator 112 to open the jaws 108. Although the example provided in FIG. 1 depicts the use of an actuator 112 to open and close jaws 108, any mechanical, electrical, or manual means may be used to open and close jaws 108. Alternate embodiments of surgical devices may include any device with opposable jaws that comprise at least one electrode on each jaw, and include both endoscopic style and open surgery style instruments, such as hemostat style devices The surgical device 102 further comprises a flexible multi-conductor cable 118 housing one or more electrical leads, and the flexible multi-conductor cable 118 terminates in a surgical device connector 120. As shown in FIG. 1, the surgical device 102 couples to controller 104, such as by a controller connector 122 on an outer surface of the enclosure 126. Surgical device 102 may deliver electrical current by way of multi-conductor cable 118 and jaws 108 during a seal cycle of the vessel sealing system.

Still referring to FIG. 1, a display device or interface device 124 is visible through the enclosure 126 of the controller 104, and in some embodiments a user may select operational modes of the controller 104 by way of the interface device 124 and related buttons 128. For example, using one or more of the buttons 128 the physician may select among modes of operation, such as a first mode which may take longer to create the seal and results in better seal strength. In some embodiments, the first mode may provide a more reliable seal across a wide range of tissues. A more reliable seal may be one that is less likely to fail when tested in the same manner as seals produced by surgical device 102 in a different mode. A second mode may seal a vessel in a manner that takes less time, possibly with lower seal strength. A third mode may be used to seal a vessel faster than the first and second modes, again with possibly lower seal strength or with a more limited vessel size sealing capability. The various modes of operation are discussed in more detail below. In some embodiments, the mode of operation may be selected by selectively depressing finger buttons present on surgical device 102 instead of or in addition to selections made through buttons 128. Finger buttons may be present on handle 110, for example. The mode of operation may also be controlled by a foot pedal assembly 130, discussed next.

In some embodiments, the vessel sealing system 100 comprises the foot pedal assembly 130. The foot pedal assembly 130 may comprise a pedal device 132, a flexible multi-conductor cable 134 and a pedal connector 136. While one pedal device 132 is shown, one or more pedal devices may be implemented. The enclosure 126 of the controller 104 may comprise a corresponding connector 138 that couples to the pedal connector 136. A physician may use the foot pedal assembly 132 to control various aspects of the controller 104, such as the mode of operation, or on-off control of the application of electrical current to surgical device 102. This embodiment of the surgical device 102 is merely an example and other embodiments of the surgical device 102 may be used to implement the methods and systems discussed. Various aspects of the jaw 108 at the distal end of forceps 106 will be discussed next.

Figure 2:
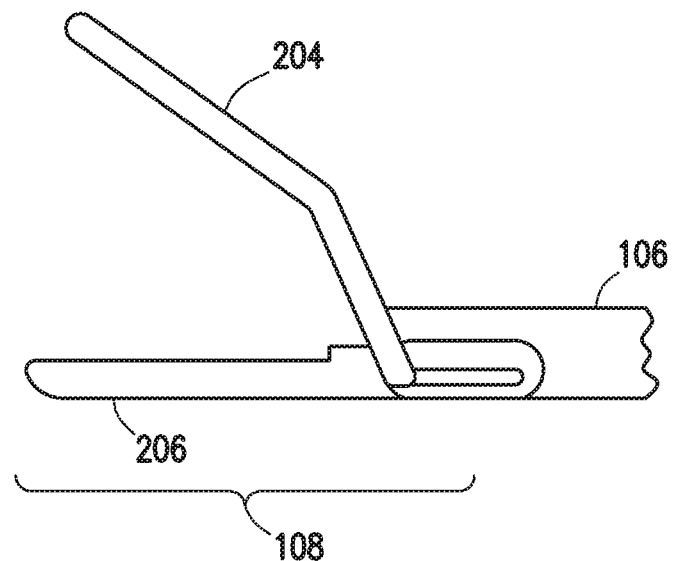
FIG. 2 shows an elevation view of energy based instrument jaws of the vessel sealing system in accordance with at least some embodiments.

FIG. 2 shows a side elevation view of exemplary jaws of the vessel sealing system in accordance with at least some embodiments. In particular, jaws 108 comprise a first jaw 204 and a second jaw 206 and a first and second electrode may be disposed on the first and second jaw respectively, each electrode electrically isolated from each other and coupled to controller 104 so as to supply energy through the target tissue disposed between the jaws. Alternatively each jaw may define an electrode, each jaw electrically isolated from each other so as to define a bipolar device. The second jaw 206 may be stationary while the first jaw 204 is rotatable/slidable.

In another embodiment, the second jaw 206 may be stationary while the first jaw 206 is rotatable. In yet another embodiment, the forceps 106 may be configured in such a way that both the first jaw 204 and second jaw 206 rotate about a common pivot point between an open orientation (i.e., where the jaws are spaced apart at the distal end of forceps 106) and a closed orientation (i.e., where the jaws are parallel). In yet another embodiment, jaws 108 may be associated with a blade to cut the tissue, where the blade selectively moves within parallel channels defined in each jaw 204 and 206.

Any mechanism or design that enables the jaws 108 to be spaced apart and brought closer together in an approximate parallel fashion may be used. More particularly jaws 108 may approach each other in such a way that electrodes associated with the jaw do not make electrical contact with each other so that energy flowing from electrodes associated with jaws 108 or energized portions of the jaw itself always flows through tissue disposed through jaws and not directly from one electrode to another. Additionally, any configuration of jaws 108 and associated mechanism may be used that enables first jaw 204 and second jaw 206 to apply substantially constant pressure to tissue held between the jaws 108 from a distal to proximate end of the jaws 108. Furthermore, any configuration of jaws 108 that provides for the ability to compress different tissues to a relatively uniform height, such that a gap between electrodes is similar across various types of tissues may be implemented in jaws 108.

Figure 3:
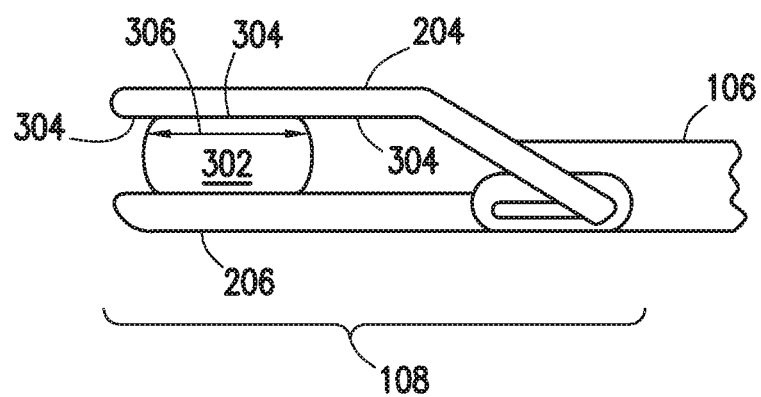
FIG. 3 shows an additional elevation view of energy based instrument jaws of the vessel sealing system in accordance with at least some embodiments.

FIG. 3, shows a side elevation view of jaws 108 with tissue between the jaws. As depicted, jaws 108 are pressed around tissue 302 comprising vessels within. In the embodiment depicted in FIG. 3, first jaw 204 is rotatable and slid into place such that a surface 304 abuts tissue 302. As depicted, jaws 108 are positioned to enable sealing of tissue 302 and/or blood vessels within tissue 302 by way of an application of electrical current administered through the jaws 108 themselves, or through electrodes defined on inside surfaces of the jaws. In order to achieve a successful seal in an efficient period of time, a power application algorithm (hereinafter "algorithm") is applied within the controller to determine an amount of electrical current to apply to the tissue 302 by way of jaws 108. In various embodiments, an amount of electrical current applied to tissue 302 is varied such that an impedance of the tissue 302 changes at one or more predetermined rates.

In order for the jaws 108 to effectively deliver electrical current to tissue 302, jaws 108 may be constructed in a manner such that jaws 108 are stiff enough to apply relatively constant pressure across the tissue mass within jaws 108. That is, jaws 108 may be constructed such that a substantially constant pressure is applied to areas of tissue 302 abutting surface 304 and a corresponding surface along second jaw 206. Jaws 108 are constructed in such a manner as to avoid causing shorts across first jaw 204 and second jaw 206 when first jaw 204 and second jaw 204 are closed around tissue 302. Overall, jaws 108 are constructed in such a manner that near constant and/or equal pressure is applied to tissue held between jaws 108 abutting surface 304 of first jaw 204 and a corresponding surface of second jaw 206.

In various embodiments, as jaws 108 apply substantially constant pressure and deliver electrical current to tissue 302, length 306 of tissue 302 may vary. Although length of tissue within jaws 108 may change in response to an application of substantially constant pressure and/or electrical current, the length is related to an amount of tissue within jaws 108. There may be an initial length of tissue prior to an application of substantially constant pressure and/or electrical current, and a length 306 after the application of substantially constant pressure and/or electrical current, but nevertheless length of tissue is correlated to amount of tissue between the jaws 108.

The modes of operation may employ a sealing technology that heats or raises the temperature of tissue located in a seal area (e.g., tissue held between jaws 108), to a temperature which is above a temperature that causes denaturation of structural proteins. During a seal cycle, a combination of pressure and an application of electrical current resulting in high temperature may cause cellular boundaries to be broken down in the tissue, and proteins may be denatured. At the end of the seal cycle a seal may be formed by a mixed protein mass. Thus, in a seal cycle a combination of pressure and an application of electrical current resulting in high temperatures cause a restructuring of tissue in the seal area.

It is noted that radio frequency (RF) coagulation shall not be considered "sealing" for purposes of the specification and claims.

In accordance with example methods, during a seal cycle the tissue 302 may undergo three conceptual phases or steps of treatment. The first is a sensing phase, the second is a heating phase, and the third is a desiccating phase. The phases are described according to phenomena experienced by the tissue 302 during a phase. For example, during the heating phase, the tissue 302 is heated. Although the seal cycle has been conceptually partitioned into a sensing, heating, and desiccating phase, it is noted that portions of tissue may be experiencing one or more of the phenomena identified by the phase descriptors. Such an occurrence does not negate the fact that tissue 302 may be in a certain phase of treatment. For example, during the sensing phase, portions of the tissue may be heated. The fact that some heating takes place does not obviate the status of "sensing." Indeed, in some embodiments, the second phase may be initiated during the first sensing phase.

During the sensing phase, an amount of tissue 302 held between jaws 108 is sensed. In particular, the jaws 108 may apply an electrical current through tissue 302 between the jaws that is varied by a controller 104 (See FIG. 1) such that a value of impedance of tissue 302 is changed at one or more predetermined rates. For example, a value of impedance of tissue 302 may be changed over time such that a rate of change of impedance of tissue 302 is about −50 Ohms/second. As such, during an example sensing phase the impedance of the tissue is driven down at a constant rate using low power (e.g., less than 5 Watts (W)). An initial decrease in impedance of tissue 302 may be associated with an increase of temperature of the tissue 302 and surrounding fluids. Thus, tissue 302 may begin to be heated during the sensing phase.

By controlling a value of impedance of tissue 302 over time during the sensing phase, an amount of tissue 302 may be sensed. For example, during the sensing phase, an amount of applied power is controlled to achieve or drive a constant rate of change of impedance of tissue 302. The mean power applied over a duration of time of the sensing phase (to achieve the constant rate of change of impedance) may be indicative of the amount of tissue 302 held between jaws 108. Larger amounts of tissue may use higher mean power to achieve the constant rate of change of impedance. Smaller amounts of tissue may use lower mean power to achieve about the same constant rate of change of impedance.

Thus a value indicating the amount of mean power applied over a duration of time (in conjunction with maintaining a constant rate of change of impedance of tissue 302) of the sensing period may be used as an output value to determine the amount of tissue 302 held between jaws 108. In various embodiments, a value indicating the amount of mean power applied (in conjunction with maintaining a constant rate of change of impedance of tissue 302) during the sensing period may also be used as an output value to determine a type of tissue (e.g. vein vs. artery) held between jaws 108.

In other embodiments, applied power may be held constant while the rate of change of impedance is measured over a period of time. The rate of change of impedance is then related to the amount of tissue 302 sensed between the jaws 108. It is noted that in calculating and measuring impedance, in one embodiment, the real and imaginary portions of the impedance are not calculated; but rather, a value indicative of the magnitude of impedance of the tissue is measured at any given time without actually determining the underlying components.

Based on the amount of tissue 302 sensed during the sensing phase, a plurality of parameters may be adjusted that are used during the heating and desiccating phases of the seal cycle. Adjusted parameters may include a targeted value of impedance of tissue at a given time (i.e., a set point impedance as a function of time) or a rate of change of impedance of tissue 302 (i.e., a first derivative of impedance as a function of time). For example, the targeted value of impedance over time may be defined by a predetermined path or trajectory of the impedance value over time. Alternatively, the target value of impedance may be defined by a targeted rate of change of the impedance value over time. Adjusted parameters may also include an amount of power to apply to tissue 302. Accordingly, controller 104 (FIG. 1) may apply an electrical current such that the a value of impedance of tissue 302 is controlled over time during the heating and desiccating phases based on information gathered during the sensing phase and/or a mode of operation selected by the operator.

During the heating phase, a varying electrical current may be applied to tissue 302 to drive a change in impedance of tissue 302 at a constant rate, until a lowest value of impedance of the tissue 302 is reached. In some embodiments, varying electrical current is applied until a lowest value of impedance of tissue 302 is reached and surpassed by a predetermined amount. During this heating phase, a change of impedance of tissue 302 may be controlled by the controller, and may be selected based on output information received regarding the amount or type of tissue 302 detected during the sensing phase and/or a mode of operation selected by an operator, such as a physician.

During the heating phase, a temperature of the tissue 302 in jaws 108 is increased to the boiling point of water or above. The conductivity of tissue 302 is a function of temperature. As the temperature of tissue 302 increases, conductivity increases and impedance decreases. As such, a change in impedance of tissue 302 may be used to estimate a change in temperature of the tissue 302. In some embodiments, the boiling point temperature may be between 120° C. and 140° C., due to an increased pressure placed on the tissue 302 by jaws 108.

In various embodiments, the tissue 302 may be heated to a temperature which is above the temperature that causes denaturation of structural protein. The combination of pressure applied by jaws 108 and increased temperature results in restructuring the tissue in a seal area defined by the portion of tissue 302 held between jaws 108. During the heating phase, tissue 302 may become thinner, extrusion may occur and tissue may fold back on itself to create a strong seal or fused portion of vessel. Additionally, some tissue desiccation may occur. The structure of tissue 302 created during the heating phase affects the overall seal strength as well as the reliability of maintaining the seal under pressure.

In controlling the heating rate of tissue 302 or alternatively, controlling the value of impedance of tissue 302 over time, an algorithm controlling an amount of electrical current applied by way of jaws 108 may account for a plurality of parameters; for example, the amount and/or type of tissue located in the jaws, the conditions of tissue in the surrounding locality, and the residual heat in the jaws. Because the amount and/or type of tissue located within jaws 108 affects the amount of electrical current needed to raise the temperature, the rate of power applied to the tissue is at least partially determined by the amount and/or type of tissue 302 located within jaws 108.

By controlling a value of impedance of tissue 302 over time, which results in control of the heating rate of tissue 302 as well, various pitfalls may be avoided. For instance, if tissue 302 is heated too quickly, vapor pockets may form which may lead to decreased seal strength. If the tissue 302 is heated too slowly, the tissue 302 may have an acceptable seal, but the sealing time may be too long and excessive thermal spread may occur. Thus, an algorithm is configured to adjust the value of impedance of tissue 302 over time, which results in control of rate of tissue temperature change, versus the overall seal time in order to achieve a stronger overall seal strength and greater seal reliability in a relatively short timeframe.

The end of the heating phase is marked by an observation of the impedance of tissue 302 no longer decreasing and instead the impedance of tissue 302 beginning to increase. Additionally, at the end of the heating phase, (where a negative rate of impedance change switches to a positive rate of impedance change) a full compression of jaws 108 may be reached in which any tissue extrusion has taken place, and a distance between electrodes is determined by the non-electrical standoff height inside jaws 108. Tissue compression may be correlated to an amount of impedance sensed. An increase in impedance may be observed due to the vaporization of water (i.e., water present in the tissue has vaporized during the heating), and reformation of proteins. The point at which the impedance of tissue 302 ceases to decrease and begins to increase marks a transition from the heating phase to the desiccating phase.

During the desiccating phase, the controller 104 may apply a varying electrical current by way of jaws 108 to tissue 302 in a manner such that a value of impedance of tissue 302 is controlled over a duration of time, predetermined by an algorithm. In some embodiments, the value of impedance of tissue 302 may be changed at a predetermined rate determined by an algorithm. In some embodiments, the predetermined rate may define one or more functions that define a particular trajectory of an impedance value of tissue 302 over time. For example, a predetermined rate may define a function that defines a linear trajectory or a parabolic trajectory of an impedance value of tissue 302 over time. In some embodiments, a predetermined rate may define one or more target rates of change of impedance value of tissue 302 over time (i.e., a target rate of change of impedance over time of tissue 302).

The algorithm may set the predetermined rate based on information gathered during the sensing phase, heating phase and/or a mode of operation selected by an operator. The desiccation phase is characterized by an upward trend in impedance in which the tissue 302 is reformed under pressure into the fused vessel sealed form. In the desiccation phase, tissue 302 may be dehydrated and proteins which were denatured during the heating phase may be recombined during the desiccation phase. A seal is created by a reformed mixed protein mass. Varying a value of impedance of tissue 302 at a predetermined rate enables the controller 104 to adjust the power delivery to different tissue types held between jaws 108, thus enabling uniform sealing of various tissues.

Taking into account a sensed amount and/or type of tissue 302 and the mode of operation, during the desiccation phase, controller 104 may change the impedance of tissue 302 based on one or more predetermined rates, hold the impedance of tissue 302 at a specified predetermined value, or drive the impedance to a certain value within a predetermined time frame or a predetermined function of time.

As an example of taking into account a sensed amount of tissue 302 and the mode of operation, a small, isolated vessel may use a low mean power value during the sensing phase, resulting in an activation of a mode of operation in which the desiccating phase lasts two seconds with a driven rate of change in impedance of 300 Ohms per second; by contrast, a large, well-hydrated tissue bundle may use a larger mean power value during the sensing phase, resulting in an mode of operation in which the desiccating phase lasts four seconds with a driven rate of change in impedance of 100 Ohms per second.

As described, in various phases of the seal cycle, an amount of electrical current to be applied to tissue 304 may be determined by the algorithm; and the amount of electrical current may be varied according to various parameters. For example, the algorithm may adjust an amount of electrical current applied to tissue 302, based on the quantity of tissue determined or sensed between the jaws 108, the composition of the tissue 302 between jaws 108, and hydration levels. In addition, the makeup and condition of tissue 302, such as fat content, collagen content, and calcification, may be determined and/or considered.

The ability to control a value of impedance of tissue 302 over time enables the surgical device 102 to produce a better quality seal in an efficient amount of time using an efficient amount of energy. By controlling the value of impedance of the tissue 302 over time during various phases of the seal cycle, the surgical device 102 is able to heat and reform tissue held between jaws 108 evenly and efficiently which results in a better seal. As the structure of tissue 302 created during the heating phase affects the overall seal strength, the controlled application of electrical current to tissue 302 during the heating phase is beneficial. A successful seal may be determined based on a burst pressure, seal structure, seal speed, extend of spread of thermal effect to surrounding tissue, vapor formation, the amount of tissue sticking to the applicator, and an amount of unwanted char on the tissue.

By controlling and adjusting the amount of power or electrical current over a period of time to the tissue 302, stronger sealing of the tissue 302 may occur without undertreating the tissue (e.g., the tissue may be non-hemostatic) or over-treating the tissue (e.g., resulting in potential charring, excessive steam formation, unintended thermal damage to tissue located outside of the jaws, and/or a weaker seal). Additional aspects of the algorithms that may be applied by the controller 104 are discussed below, after discussion of an example controller 104.

Figure 4:
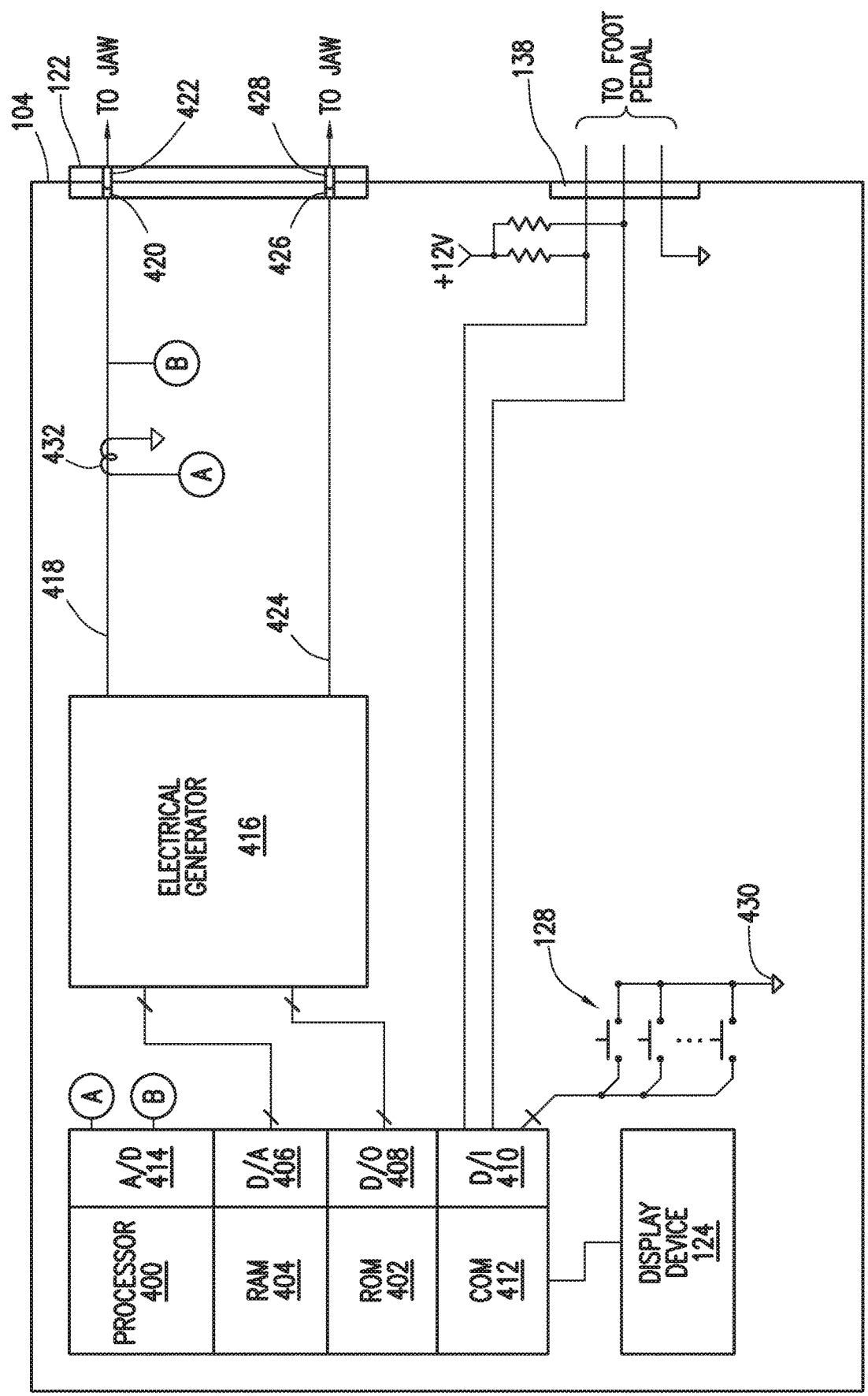
FIG. 4 shows an electrical block diagram of a controller in accordance with at least some embodiments.

FIG. 4 shows an electrical block diagram of controller 104 in accordance with at least some embodiments. In particular, the controller 104 comprises a processor 400. The processor 400 may be a microcontroller, and therefore the microcontroller may be integral with read-only memory (ROM) 402, random access memory (RAM) 404, digital-to-analog converter (D/A) 406, analog-to-digital converter (ND) 414, Digital output (D/O) 408, and digital input (D/I) 410. The processor 400 may further provide one or more externally available peripheral buses, such as a serial bus (e.g., I²C), parallel bus, or other bus and corresponding communication mode.

The processor 400 may further be integral with communication logic 412 to enable the processor 400 to communicate with external devices, as well as internal devices, such as display device 124. Although in some embodiments the processor 400 may be implemented in the form of a microcontroller, in other embodiments the processor 400 may be implemented as a standalone central processing unit in combination with individual RAM, ROM, communication, ND, D/A, D/O, and D/I devices, as well as communication hardware for communication to peripheral components.

ROM 402 stores instructions executable by the processor 400. In particular, the ROM 402 may comprise a software program that, when executed, causes the controller 104 to implement two or more modes of operation of the surgical device 102.

The RAM 404 may be the working memory for the processor 400, where data may be temporarily stored and from which instructions may be executed. Processor 400 couples to other devices within the controller 104 by way of the digital-to-analog converter 406 (e.g., in some embodiments the electrical generator 416), digital outputs 408 (e.g., in some embodiments, the electrical generator 416), digital inputs 410 (e.g., interface devices such as push button switches 128 or foot pedal assembly 130 (FIG. 1)), and communication device 412 (e.g., display device 124).

Electrical generator 416 generates an alternating current (AC) voltage signal. Electrical generator 416 may define an active terminal 418 which couples to electrical pin 420 in the controller connector 122, electrical pin 422 in the surgical device connector 102, and ultimately to jaws 108 (FIG. 3). The active terminal 418 is the terminal upon which the voltages and electrical currents are induced by the electrical generator 416, and the return terminal 424 provides a return path for electrical currents. In some embodiments, active terminal 418 may couple to first jaw 204 (FIG. 2), while return terminal 424 couples to second jaw 206 (FIG. 2). Thus, electrical generator 416 provides controllable electrical current to jaws 108. Electrical generator 416 enables controller 104 to vary electrical current flowing through tissue 302 (FIG. 3) such that impedance of the tissue 302 changes at a given rate.

It would be possible for the return terminal 424 to provide a common or ground being the same as the common or ground within the balance of the controller 104 (e.g., the common 430 used on push buttons 128), but in other embodiments, the electrical generator 416 may be electrically "floated" from the balance of the controller 104, and thus the return terminal 424, when measured with respect to the common or earth ground (e.g., common 430) may show a voltage. However, an electrically floated electrical generator 416 and thus the potential for voltage readings on the return terminal 424 relative to earth ground does not negate the return terminal status of the terminal 424 relative to the active terminal 418.

The AC voltage signal generated and applied between the active terminal 418 and return terminal 424 by the electrical generator 416 may be RF energy in the form of a sine wave with variable peak-to-peak voltage; a square wave with variable peak-to-peak voltage; a square wave with a variable duty cycle; a square wave with variable peak voltage and variable duty cycle.

In some embodiments, the various modes of operation implemented by the controller 104 may be controlled by the processor 400 by way of digital-to-analog converter 406. For example, the processor 400 may control the output voltages by providing one or more variable voltages to the electrical generator 416, where the voltages provided by the digital-to-analog converter 406 are proportional to the voltages to be generated by the electrical generator 416. In other embodiments, the processor 400 may communicate with the electrical generator 416 by way of one or more digital output signals from the digital output converter 408, or by way of packet-based communications using the communication device 412.

Still referring to FIG. 4, in some embodiments the controller 104 further comprises a mechanism to sense the electrical current provided to the tissue within the jaws which enables the controller 104 to measure an impedance of the tissue disposed between the jaws. A value indicative of electrical current provided to the tissue may be provided by current sense transformer 432. In particular, current sense transformer 432 may have a conductor of the active terminal 418 threaded through the transformer such that the active terminal 418 becomes a single turn primary. Current flow in the single turn primary induces corresponding voltages and/or currents in the secondary. Thus, the illustrative current sense transformer 432 is coupled to the analog-to-digital converter 414 (as shown by the bubble A). In some cases, the current sense transformer may couple directly to the analog-to-digital converter 414, and in other cases additional circuitry may be imposed between the current sense transformer 432 and the analog-to-digital converter 414, such as amplification circuits and protection circuits. For example, in one example system the current sense transformer 432 is coupled to an integrated circuit device that takes the indication of current from the current sense transformer 432, calculates a root-mean-square (RMS) current value, and provides the RMS current values to the processor 400 through any suitable communication system (e.g., as an analog value applied to the ND 414, as a digital value applied to the multiple inputs of the D/I 410, as a packet message through the communication port 412).

The current sense transformer 432 is merely illustrative of any suitable mechanism to sense the current supplied to the tissue, and other systems are possible. For example, a small resistor (e.g., 1 Ohm, 0.1 Ohm) may be placed in series with the active terminal 418, and the voltage drop induced across the resistor used an indication of the electrical current.

Given that the electrical generator 416 is electrically floated, the mechanism to sense current is not limited to the just the active terminal 418. Thus, in yet still further embodiments, the mechanism to sense current may be implemented with respect to the return terminal 424. For example, illustrative current sense transformer 432 may be implemented on a conductor associated with the return terminal 424.

In some example systems, the feedback parameter used by the processor 400 regarding the electrical generator 416 is the electrical current flow. For example, in systems where the electrical generator can accurately produce an output voltage independent of the impedance of the attached load, the processor 400 having set point control for the voltage created by the electrical generator 416 may be sufficient (e.g., to calculate a value indicative of impedance of the tissue). However, in other cases, voltage too may be a feedback parameter. Thus, in some cases the active terminal 418 may be electrically coupled to the analog-to-digital converter 414 (as shown by bubble B).

However, additional circuitry may be imposed between the active terminal 418 and the analog-to-digital converter 414, for example various step-down transformers, protection circuits, and circuits to account for the electrically floated nature of the electrical generator 416. Such additional circuitry is not shown so as not to unduly complicate the figure. In yet still other cases, voltage sense circuitry may measure the voltage, and the measured voltage values may be provided other than by analog signal, such as by way of packet-based communications over the communication port 412.

Figure 5:
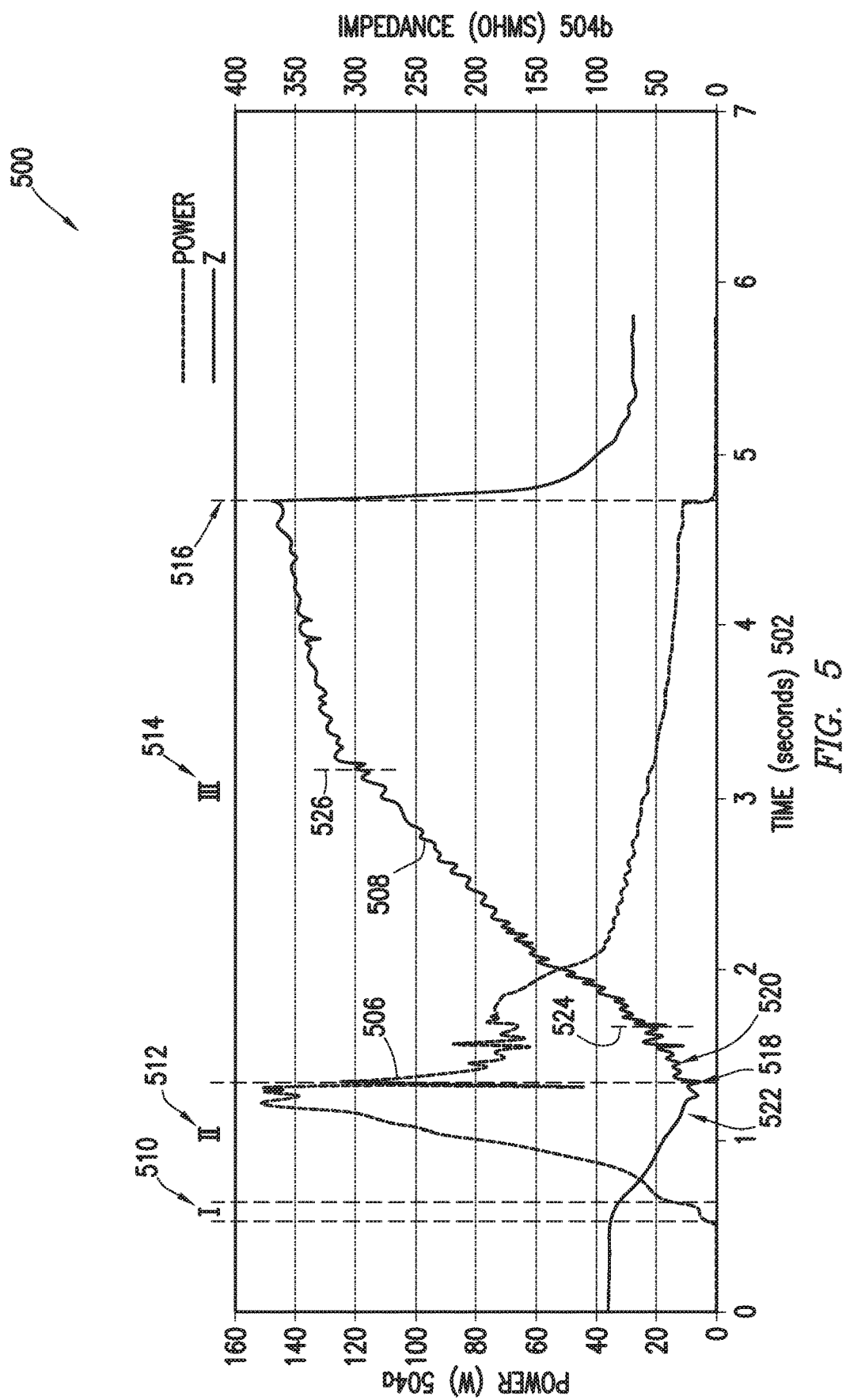
FIG. 5 shows an example graph depicting an amount of power applied to a tissue as well as an impedance of the tissue over time during a seal cycle of the vessel sealing system in accordance with at least some embodiments.

The specification now turns to a more detailed discussion of the various phases that may occur during a seal cycle. FIG. 5 depicts an example graph 500 depicting an amount of power (shown by line 506) applied to tissue over time during an example seal cycle. Time is plotted along the x-axis 502 while a power applied to the tissue is plotted along the y-axis 504a. Superimposed in the graph is also a line depicting the change in impedance over time (shown by line 508) of tissue between jaws, values associated with the impedance are shown along a second y-axis 504b. Thus, a correlation between the amount of power applied to the tissue and the change of impedance of the tissue over time may be seen.

The sensing phase 510, is shown approximately in section I; the heating phase 512 is approximately shown in section II; and the desiccating phase 514 is shown approximately in section III. Sensing phase 506 is relatively short and may last approximately 100 milliseconds. As depicted on line 506, the sensing phase initially starts using low power (e.g., less that 5 W), however the power level is not limited to amounts lower than 5 W. The corresponding line 508 demonstrates that during the application of power, the impedance of the tissue is driven down. That is, the controller adjusts the power output so as to drive the impedance of the tissue between jaws down at a constant rate, using low power. Some heating may begin during the sensing phase 506, but the overall aim during the sensing phase 506 is to sense an amount or type of tissue between the jaws.

During the heating phase 512, the amount of power applied over time is increased. At the end of the heating phase 508, the highest amount of power applied may generally coincide with reaching the lowest value of impedance of tissue 302. However, the highest amount of power applied and reaching the lowest value of impedance of tissue 302 may not occur at the same time. The lowest value of impedance of tissue 302 may vary based on the height of electrode separation, type of tissue 302 in the jaws, or an amount of the electrode surface area.

Prior to reaching the lowest value of impedance of tissue between the jaws, an increase in rate of change of power may be used to increase the rate of change of the impedance (e.g., to go from −50 Ohms/sec to −100 Ohms/sec). Likewise prior to reaching the lowest value of impedance of tissue between the jaws, a decrease in the rate of change of power may be used to decrease the rate of change of impedance (e.g., to go from −100 Ohms/sec to −50 Ohms/sec). Thus, during the heating phase 512, an application of increased power to tissue 302 between the jaws results in a faster drop in impedance. However, the faster the impedance drops during the heating phase, the less likely that uniform heating of tissue between the jaws occurs. The less likely that uniform heating has occurred, the less ideal is the final tissue structure created during the heating phase and the less likely one is to achieve a stronger seal.

When the seal cycle transitions from the heating phase 512 to the desiccating phase 514, there is a reversal of system dynamics between heating phase 512 and desiccating phase 514. For example, during the heating phase 512 an increase in the power to the tissue causes the impedance of the tissue to decrease impedance at a faster rate, while in the desiccating phase 514 an increase in power causes the impedance to increase at a faster rate. This reversal of system dynamics results in a control structure changing the controller gains. Detecting that tissue has reached a lowest value of impedance 518 is beneficial as this may determine when the control structure changes.

If the detection of the lowest value of impedance 518 occurs too late (e.g., point 520), the output power may increase too quickly and result in over-desiccation of small quantities of tissue. In situations where over-desiccation occurs exterior layers of the tissue increases bulk impedance of the tissue, lowering power output by the controller, and preventing power application to the durable interior layers of the vessel that benefit from power application as the power application to the durable interior layers reforms the vessel into a homogenous seal. If the detection occurs too early (e.g., point 522), the system may reduce the power too quickly, resulting in a longer seal cycle. Thus it is beneficial to determine when a lowest impedance is reached. In various embodiments, during the heating phase 512, impedance may be calculated periodically. Due to pockets of moisture and differences in tissue type impedance, an impedance of tissue is not necessarily a smoothly varying measurement or value. Thus a controller 104 may implement certain methods such as applying an adjustment factor to determine that a minimum in impedance value has been reached. Use of the adjustment factor may ensure transitions between control structure changes occur at an appropriate time between the transition from the heating phase 512 to desiccating phase 514.

To determine a point in time to change the control structure, a controller 104 may identify when the impedance of tissue between jaws starts to increase. As the impedance decreases during the heating phase 512, the controller 104 may track and store the lowest impedance observed at point 518. As the impedance begins to increase, the controller 104 may compare the most recent measured impedance to the lowest impedance, multiplied by an adjustment factor.

As discussed previously, the impedance of tissue is not necessarily a smoothly varying measurement and thus the impedance of a tissue may be periodically calculated. The use of the adjustment factor ensures that the lowest impedance has been reached before transitioning to the desiccating phase 514. As impedance may vary at any given time, it may be difficult to identify when the lowest impedance has been reached. For example, a first impedance value measured at a first point in time may be lower than a second impedance value measured at a second, subsequent point in time. However, the second impedance value being higher than the first impedance value may not be a good indicator of whether the impedance of the tissue between the jaws has reached the lowest impedance and begun an ascending trend. That is, an impedance value may seem to be rising in a given locality (defined by a narrow window of time), but a general trend of the impedance value may still be decreasing. An adjustment factor provides a threshold that a controller may monitor for before determining that the lowest impedance of a tissue between jaws has been reached.

In one embodiment, the adjustment factor may be in the range of 1.1-20. For example, if the controller 104 measures the real part or magnitude of the minimum impedance to be 30 Ohms, and the adjustment factor is 1.5, the controller 104 will change control structures and gains when the impedance reaches 45 Ohms (i.e., 30 Ohms*1.5). The adjustment factor may be a function of mode selection or values determined during the sensing phase 510. For example, a larger adjustment factor may be used in a mode that generates a seal faster than other modes.

After the heating phase 512 ends, the desiccating phase 514 begins (i.e., the impedance of the tissue between the jaws begins to increase). At a time 516 the desiccating phase ends application of power defined as when the impedance of tissue reaches a predetermined value. Desiccating phase 514 is characterized by an upward trend in impedance. Although an upward trend in an approximate linear fashion is depicted in graph 500, any function may be used during any phase of the seal cycle so long as the value of impedance of the tissue between jaws is controlled. Any function may be used that is effective in producing a good quality seal.

In some embodiments, during the desiccating phase 514, power applied to the tissue is decreased over time to maintain one or more predetermined rates of change of impedance of tissue between the jaws. For example, in desiccating phase 514, three different slopes of line 508 may be observed. From the beginning of desiccating phase 514 to about location 524, the rate of change of impedance is at one predetermined rate. The predetermined rate may be defined by a predetermined path or trajectory of the impedance value over time, or the predetermined rate may be defined as a first derivative of the value of impedance over time. Next, between points 524 and 526, a different predetermined rate may be used to control a value of impedance of tissue between jaws over time, depicted by a line having a different slope than the previous portion before point 524. From point 526 until the end of the desiccating phase 514, a third predetermined rate may be used to control the value of impedance of tissue between jaws over time.

The end of the desiccating phase 514 may be reached when a determination is made that the impedance of the tissue has reached a predetermined value. This predetermined value may be determined by feedback sensed during the sensing phase, or any other prior phase of the respective seal cycle. In some embodiments, the application or power may be ceased depending on other factors. For example, a final phase may be defined as a period in which zero change in impedance is observed. The impedance of tissue may be driven high and the held at a particular value in order to implement a slowly tapering application of power. In this example, a length of time (in seconds) may be defined during which there is zero change of impedance, where the length of time is defined based on parameters collected during earlier phases of the respective seal cycle.

During the desiccating, heating, and sensing phases, in several embodiments, a predetermined rate may be defined by a set point impedance as a function of time, where the set point impedance as a function of time has the predetermined path or the predetermined rate. The predetermined rate of change may be defined by a predetermined path for the portion of line 508 within the desiccating phase 514. In other embodiments, the predetermined rate may be driven such that a first derivative of the impedance as a function of time is the predetermined rate. In various embodiments, the predetermined rates of change may be determined based on information gathered during earlier phases of the seal cycle such as the sensing phase 510 or heating phase 512.

In various embodiments, a predetermined rate used during the heating and desiccating phases may be a factor of sensed variables during the sensing phase of the respective seal cycle. The predetermined rate may be based on a combination of sensed variables during the sending phase of the respective seal cycle as well as chosen parameter reflecting a mode of operation.

Lesser power is needed further along in the desiccating phase 514 to maintain a constant rate of change of impedance in the tissue. During the desiccation phase 514, an increase in power applied to tissue between the jaws results in a faster increase in impedance of tissue between the jaws. An increase of power may be applied to tissue to increase the rate of change of impedance (e.g., from 50 to 100 Ohms/sec).

Figure 6:
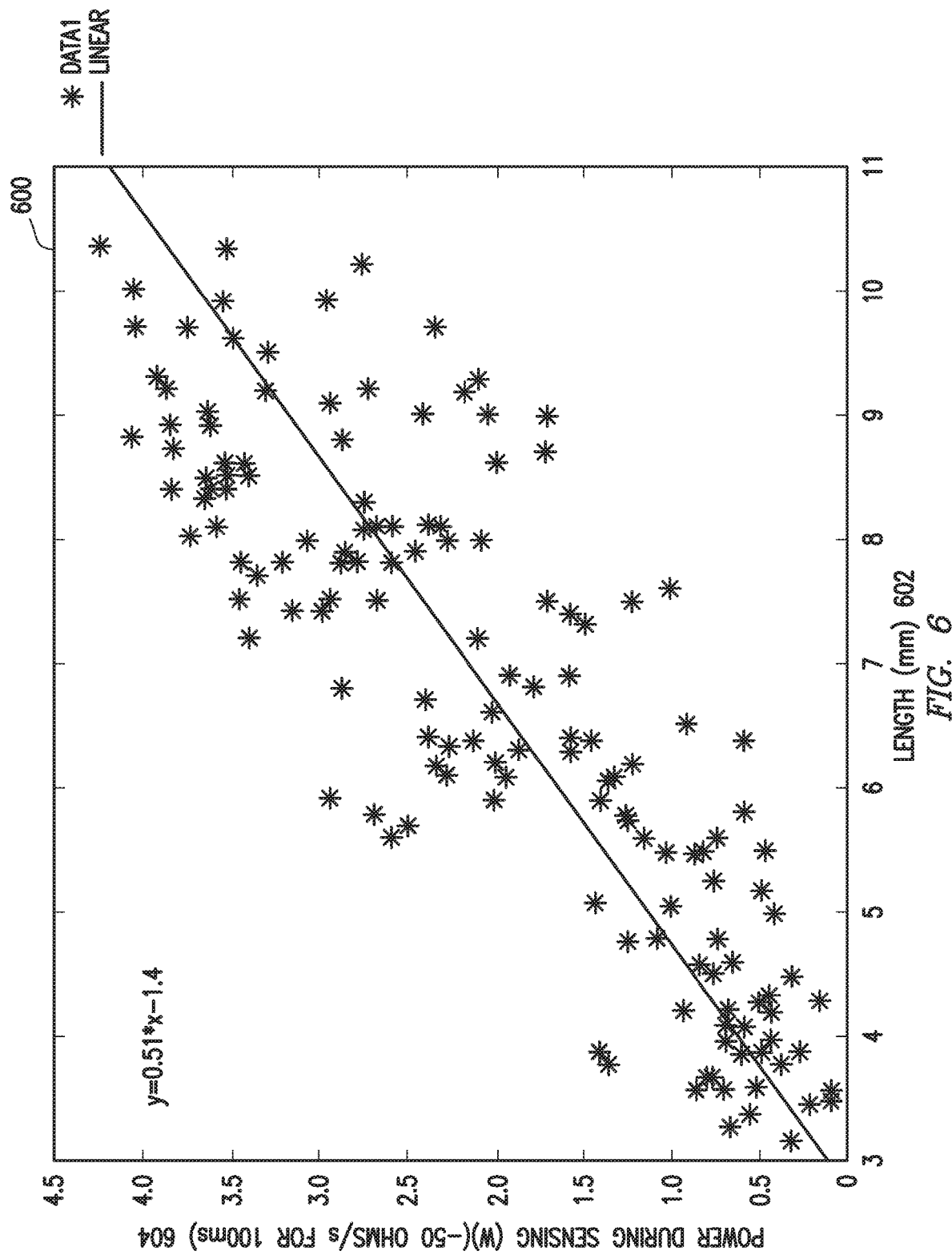
FIG. 6 shows an example graph relating length of a vessel within jaws of energy based instrument and power during sensing in accordance with at least some embodiments.

FIG. 6 shows an example graph 600 relating length of tissue between jaws and power during sensing in accordance with at least some embodiments. Data depicted in FIG. 6 illustrate lab results that confirm the correlation between a length of tissue in the jaws (as a proxy for amount of tissue) and power during the sensing phase delivered such that impedance changes at a predetermined rate. More specifically, the y-axis 604 depicts an amount of power applied to tissue during sensing such that a rate of change of impedance in the tissue occurs at −50 Ohms/sec over the first 100 milliseconds (i.e., sensing phase). The axis 602 shows the length of the tissue held between jaws, where the length of the tissue represents the length of the tissue from the distal end to the proximate end of jaws 108. In other embodiments, the quantity of tissue may be determined by the thickness of the tissue, or by other determined and/or measured characteristics of the tissue.

FIG. 6 confirms a correlation between an amount of tissue and an amount of power that may be used to drive a change of impedance within the tissue bundle over time. For example, a lower amount of power is used to drive a value of impedance over time at a rate of −50 Ohms/sec for smaller amounts of tissue than what is used for larger amounts of tissue. Such a correlation may be used to determine amount of tissue held between jaws during a sensing phase of the seal cycle.

Figure 7:
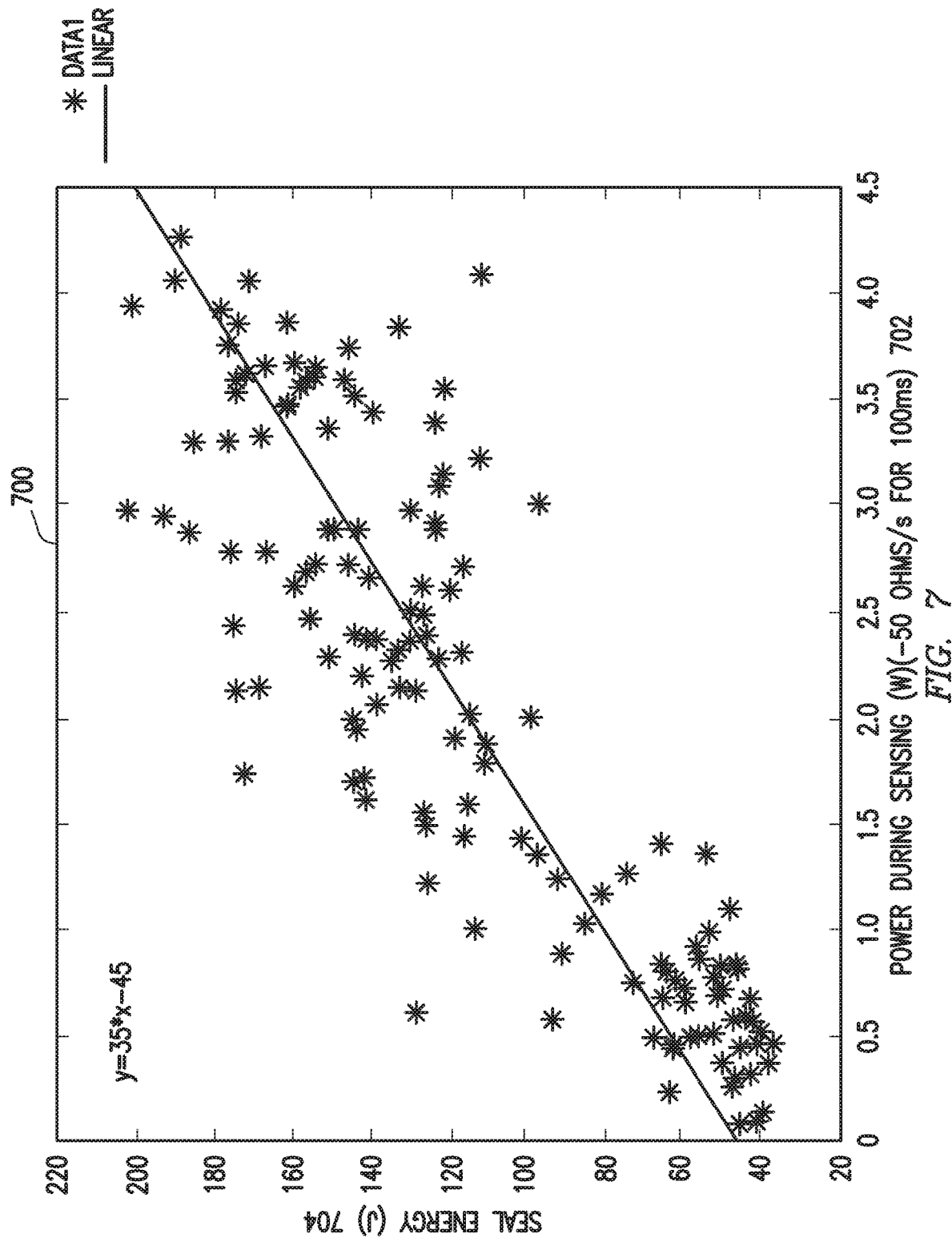
FIG. 7 shows an example graph relating power during sensing and seal energy in accordance with at least some embodiments.
Figure 8:
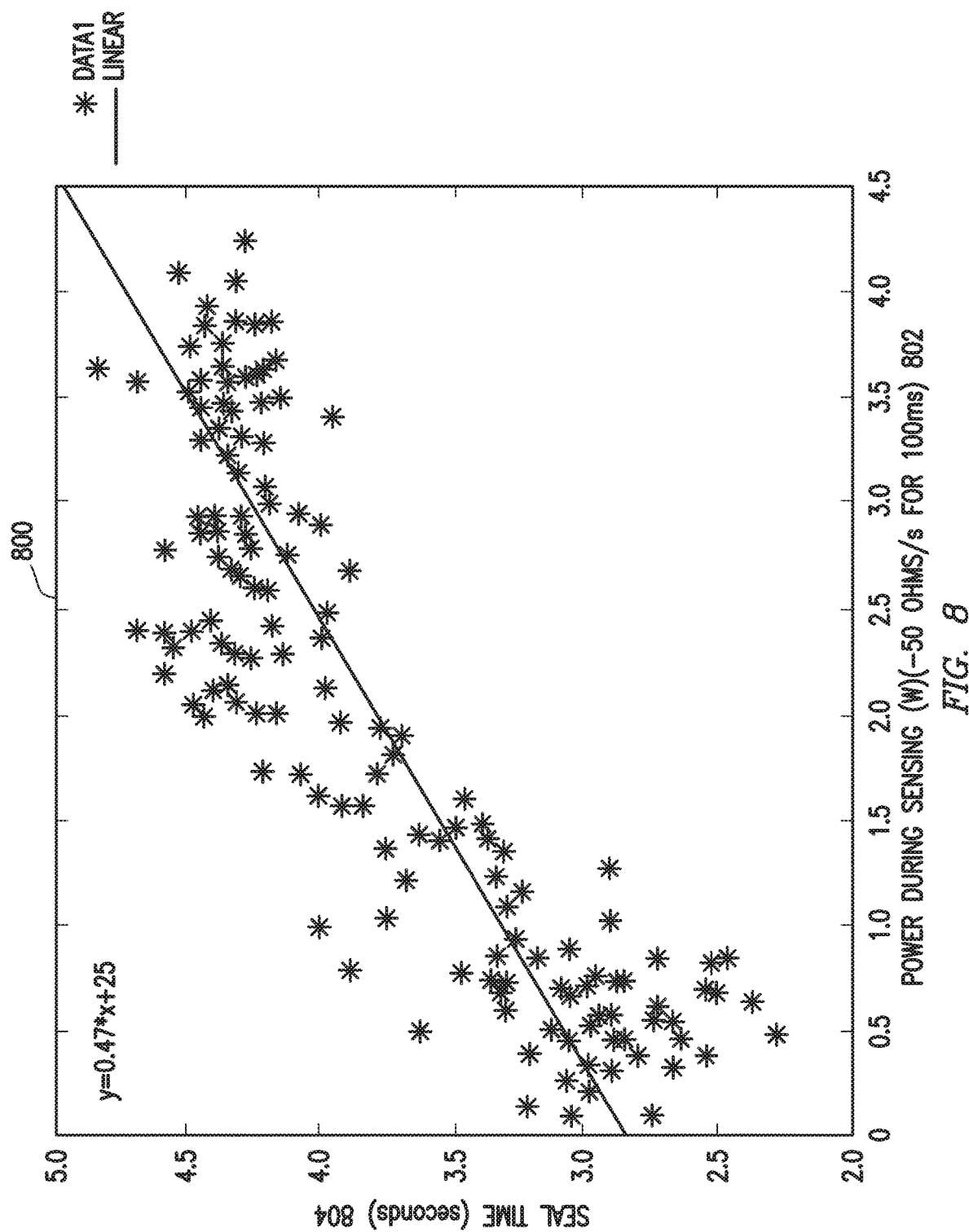
FIG. 8 shows an example graph relating power during sensing and seal time in accordance with at least some embodiments.

FIGS. 7 and 8 illustrate two graphs 700 and 800, respectively, showing data obtained in one mode of operation of the surgical device 102 (FIG. 1). In one example embodiment, graph 700 illustrates sensed Mean Power (in Watts) 702 versus the changes in an amount of delivered seal energy (in Joules) 704. Graph 700 demonstrates a correlation between an amount of power applied during the sensing phase of a seal cycle and an amount of delivered seal energy for respective tissue bundles. That is, the more power used during the sensing phase of the seal cycle of a particular tissue, the more seal energy delivered to the tissue to achieve the seal. The change in seal energy is a function of the various parameters that the algorithm adjusts based on the measured mean power during the sensing phase.

Similarly, graph 800 illustrates mean power applied during the sensing phase of a seal cycle for respective tissue bundles 802 versus seal time 804 (in seconds). Graph 800 demonstrates a correlation between the amount of time used to seal a tissue bundle and the amount of power applied during the sensing phase of the seal cycle for that particular tissue. For example, tissue that used more power to drive a change of impedance at a predetermined rate also took longer to seal. The change in seal time is a function of the various parameters that the algorithm adjusts based on the measured mean power during the sensing phase. Data collected for graphs 700 and 800 were obtained during a mode of operation that may be similar to a mode 2 as described herein. As discussed previously, the surgical device 102 may operate in various modes configured to optimize various aspects and results of the seal cycle as well as the created seal.

The specification now turns to a more detailed description of the various modes of operation of the surgical device 102. In some cases, the mode of operation may be set by the surgical device 102 based on a detected or sensed amount of tissue. Alternatively, the mode of operation may be selected by an operator. In yet still other embodiments, the mode may be selected by the controller 104 and then adjusted by the operator, if needed. Further still, an operator may choose the mode of operation but the vessel sealing controller 104 may provide suggestions or automatically change the mode. For example, if during the sensing phase, a determination is made that tissue is too large for a successful seal in a mode of operation chosen by the operator, the controller 104 may automatically switch modes and alert the physician via a sound or visual indicator on interface device 124 (FIG. 1) that a different mode is suggested. In other embodiments, the vessel sealing system 100 may override a mode of operation initially selected by the operator.

Figure 9A:
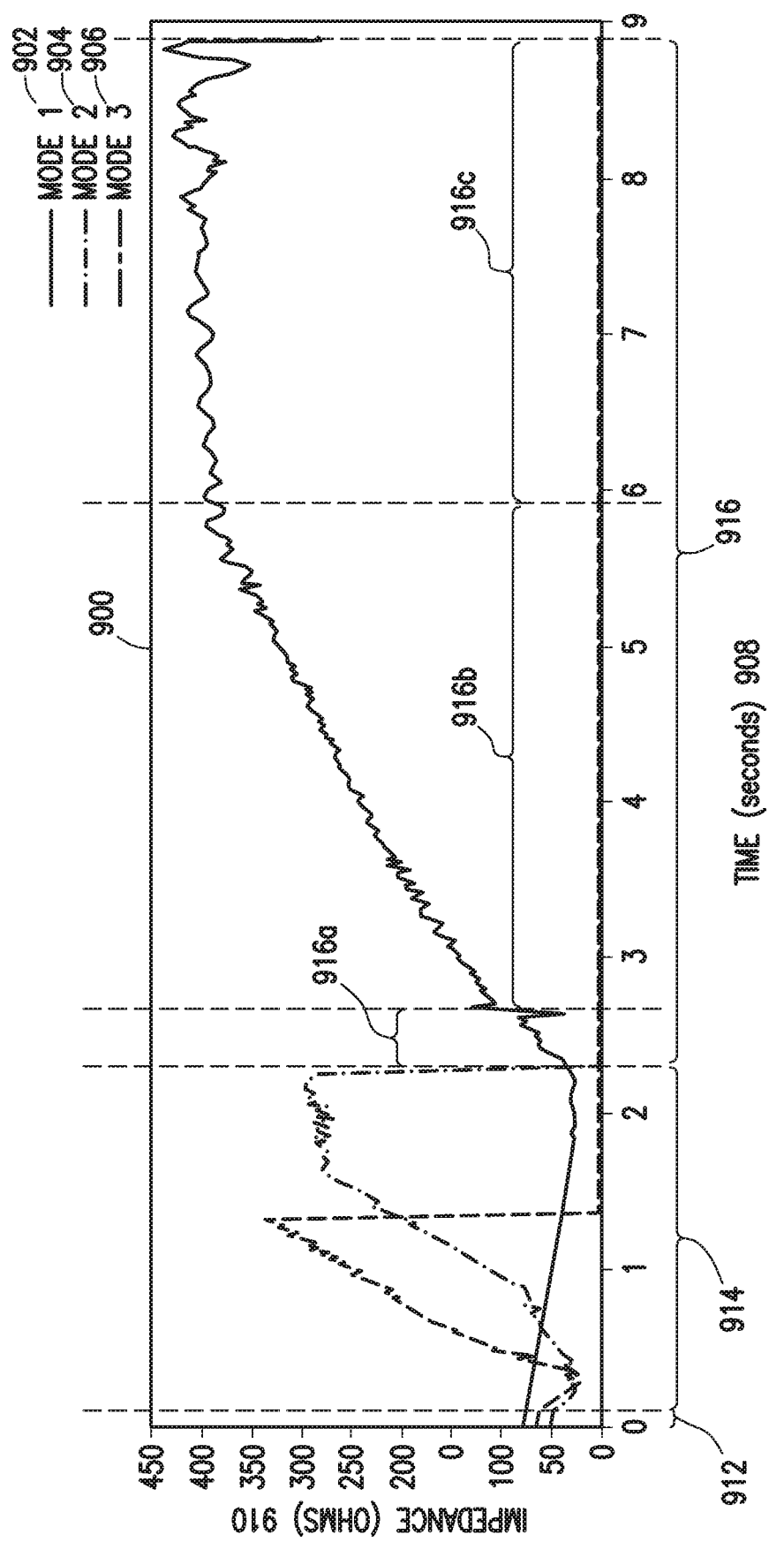
FIG. 9a shows an example graph relating a change in impedance of a tissue over time undergoing treatment by way of the vessel sealing system in accordance with at least some embodiments.
Figure 9B:
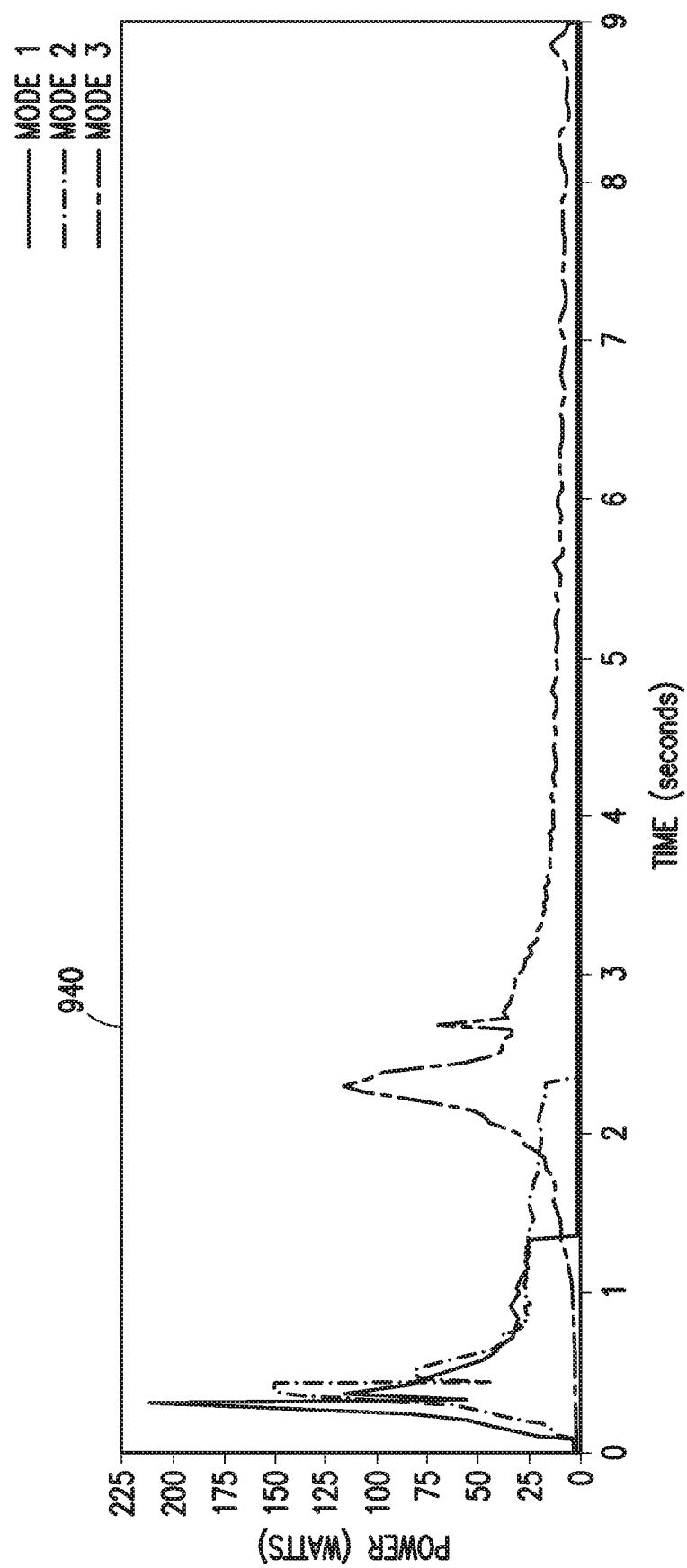
FIG. 9b shows an example graph relating an amount of power applied to a tissue over time.

FIGS. 9a and 9b correspond to each other but show different aspects of a seal cycle performed by the surgical device 102 in three different modes. Turning now to FIG. 9a, a graph 900 shows impedances for an example mode 1 (902) (shown as a solid line), mode 2 (904) (shown as a dash-dot line), and mode 3 (906) (shown as a dashed line) over respective seal cycles. In FIG. 9a, along the x-axis 908, time (in seconds) is shown and along the y-axis 910, impedance values (in Ohms) are shown. FIG. 9b shows an example graph 940 of the power applied to tissue during mode 1 (shown as a solid line), mode 2 (shown as a dash-dot line and offset slightly to the right so as to be shown more clearly), and mode 3 (shown as a dashed line) over the respective seal cycle. In graph 940, along the x-axis 942, time (in seconds) is shown and along the y-axis 944, power values (in Watts) are shown. Each of the modes 1, 2, and 3 may begin with a sensing phase comprising similar parameters. In some embodiments, a controller may apply an identical sensing phase regardless of a mode that the surgical device 102 is being operated in. Subsequent to the sensing phase, the controller may then branch to a different mode of operation based on readings obtained during the sensing phase.

For example, the sensing phases of each of the modes may spend the same amount of time in the sensing phase, and drive the impedance of the tissue between jaws at about the same rate of change of impedance. Based on readings obtained during the sensing phase, a controller may then determine which mode to operate in. Each of the modes 1, 2, and 3 may use information obtained from the sensing phase to adapt parameters used in the heating and desiccating phases. In mode 1, there is a slower rate change of impedance during the heating and desiccation phases, and the slower rate of change of impedance increases the total amount of energy delivered to the tissue between jaws; a lower amount of electrical current is applied over a longer time. In mode 3, there is a faster rate of change of impedance in the tissue during the heating and desiccation phases, which enables mode 3 to seal with less energy and shorter time.

With regards to mode 1 in 900, example durations of the sensing, heating and desiccating phases are shown. For example, duration 912 approximately depicts a sensing phase. Duration 914 approximately depicts a heating phase of mode 1, and duration 916 depicts a desiccating phase for mode 1. Within desiccating phase 916, a controller may drive one or more rates of change of impedance of tissue held between jaws. For example, duration 916a may have one rate of change of impedance that is different from a rate of change of impedance during duration 916b. Additionally, duration 916b may have a rate of change of impedance that is different than rates of changes of impedance during durations 916a and 916b.

As depicted, mode 1 may have the longest seal cycle. Mode 1 may be used in situations where a physician is more concerned with hemostasis. Mode 1 may be used for tissue bundles, fatty tissues, and large vessels. Seal cycles in mode 1 may be slower and use more energy than modes 2 and 3, however, seals resulting from a seal cycle in mode 1 may be stronger (higher average burst pressure) and more reliable (lower burst pressure standard deviation and higher reliability). Due to longer seal cycle time, there is more thermal effect and more desiccation. In some embodiments, the time to seal tissue in mode 1 may take 6-9 seconds.

For illustrative purposes some parameters that may be used in mode 1 are discussed. The heating phase of the seal cycle in mode 1 may target or control the power delivery so as to cause an impedance rate of − (negative) 50 Ohms/sec to gradually raise the temperature of the tissue between the jaws, increasing overall power delivery to the tissue during this time. During the desiccation phase of the seal cycle in mode 1, the rate of change or rate of increase of the impedance of tissue may be varied between about 50 to 75 Ohms/sec, and the overall desiccation phase may last between about 6 and 8 seconds.

In mode 2 (904), the controller 104 may adapt the heating and desiccation phases for use with a wider range of tissues. In one embodiment, a seal cycle performed in mode 2 may last 3 to 5 seconds. Compared to mode 3, mode 2 uses more energy and there is more thermal spread. In one embodiment, during the mode 2, the heating phase drives impedance down of tissue 302 between jaws at a rate of 150 Ohms/sec, limiting power that may be used during the heating phase to 150 Watts. In mode 2, during the desiccating phase, the rate of change or increase of impedance may vary from about 100 Ohms/sec to 300 Ohms/sec as a linear function of the mean power in the sensing phase. The wide variance in change of impedance over time enables the treatment of a wider range of tissues during the use of mode 2.

Mode 3 (906) enables an operator to move quickly through tissues where maximum hemostasis is not the primary concern, or large vessels are not anticipated. Power applied to the tissue is reduced in mode 3, while using less energy to generate the seal. The overall procedure time may be reduced by using mode 3, resulting in a seal cycle of approximately 1-2 seconds. Mode 3 uses the least amount of energy of all three example modes, and the heat on the distal end of the jaws 108 (FIG. 1) is reduced compared to the other example modes. There is lower thermal spread (e.g., unwanted thermal damage to adjacent tissues). In some embodiments, use of lower total power may also reduce residual temperature of the jaws thus reducing the likelihood of latent heat present on the jaws that could be dangerous if a physician uses the surgical device to manipulate unsealed tissue while the surgical device is still hot from a previous seal cycle.

In one example, in mode 3, the heating phase may drive the impedance of tissue between jaws down at a rate of −300 Ohms/sec. The allowable power during mode 3 is also higher than the other two example modes (e.g., 250 W). The change of impedance over time during the desiccating phase in mode 3 is also higher than the other two example modes (e.g., varying between about 150 Ohms to 250 Ohms).

Each seal cycle in mode 3 ends at a uniform impedance threshold, which may or may not vary as a function of an amount of power applied during the sensing phase or other calculated parameters from the sensing or heating phase. The desiccating phase is also shorter when compared to the other two example modes. As discussed previously, in some instances, the controller 104 may make a determination that the currently selected mode is not an efficient or appropriate mode. For example, if an operator, such as a physician, is using mode 3 on a large tissue bundle where a good seal in unlikely to be created, and the power applied to the tissue during the sensing phase is above a predetermined threshold, the controller 104 may automatically switch over to either mode 2 or mode 3, while alerting the operator. In another embodiment, the operator may not be alerted and as such a type of automated mode is enabled that allows switching among the three example modes as determined by the controller 104.

Figure 10:
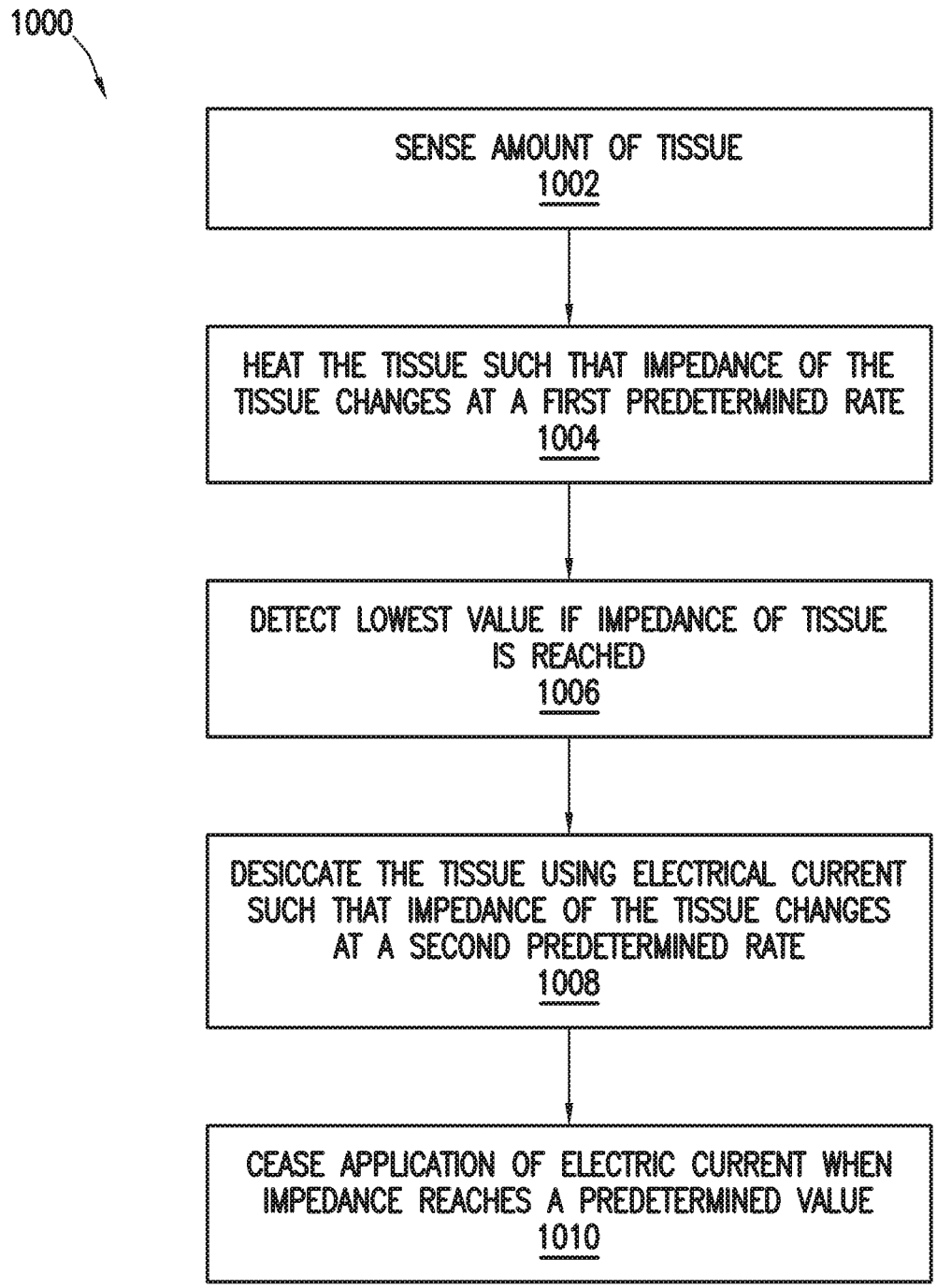
FIG. 10 shows a method in accordance with at least some embodiments.

Turning now to FIG. 10, an example method is discussed in accordance with at least some embodiments. The method generates a seal in a tissue that is held between jaws of a surgical device. In various embodiments, some of the blocks shown in FIG. 10 may be performed concurrently, in a different order than shown, or omitted. Additional method elements may be performed as desired.

Initially an amount of tissue present between jaws is sensed (step 1002). As discussed, this might occur during the sensing phase of the seal cycle. During the sensing phase, a value of the impedance of the tissue is changed in a controlled manner. And data collected during this controlled change in impedance of the tissue may be used in subsequent phases in the respective seal cycle to define various parameters used in the phases of the seal cycle. Next the tissue held between the jaws may be heated such that the impedance of the tissue changes at a first predetermined rate (step 1004). In various embodiments, this might occur during the heating phase of the seal cycle. During the heating cycle, the impedance of the tissue held between the jaws is driven down at a constant or predetermined rate.

Next the vessel sealing system may detect that a lowest value of impedance of the tissue was reached (step 1006). At this juncture, the vessel sealing system may change control systems in preparation of beginning the next phase in the seal cycle. At this step an adjustment factor as discussed above, may be used to determine that a lowest value of impedance of tissue was reached. Next the desiccating phase begins and the jaws may desiccate the tissue using electrical current such that impedance of the tissue changes at a second predetermined rate (step 1008). In various embodiments, the impedance of the tissue is driven up at one or more predetermined rates. As discussed previously, a predetermined rate may define one or more functions that define a particular trajectory of an impedance value of tissue 302 over time. For example, a predetermined rate may define a function that defines a linear trajectory or a parabolic trajectory of an impedance value of tissue 302 over time. In some embodiments, the predetermined rate may define one or more target rates of change of impedance value of tissue 302 over time (i.e., a first derivative of impedance values of tissue over time).

Finally the application of electrical current is ceased when an impedance reaches a predetermined value, determined by parameters sensed earlier in the seal cycle (step 1010). At this point a seal is generated within the tissue held between the jaws.

Figure 11:
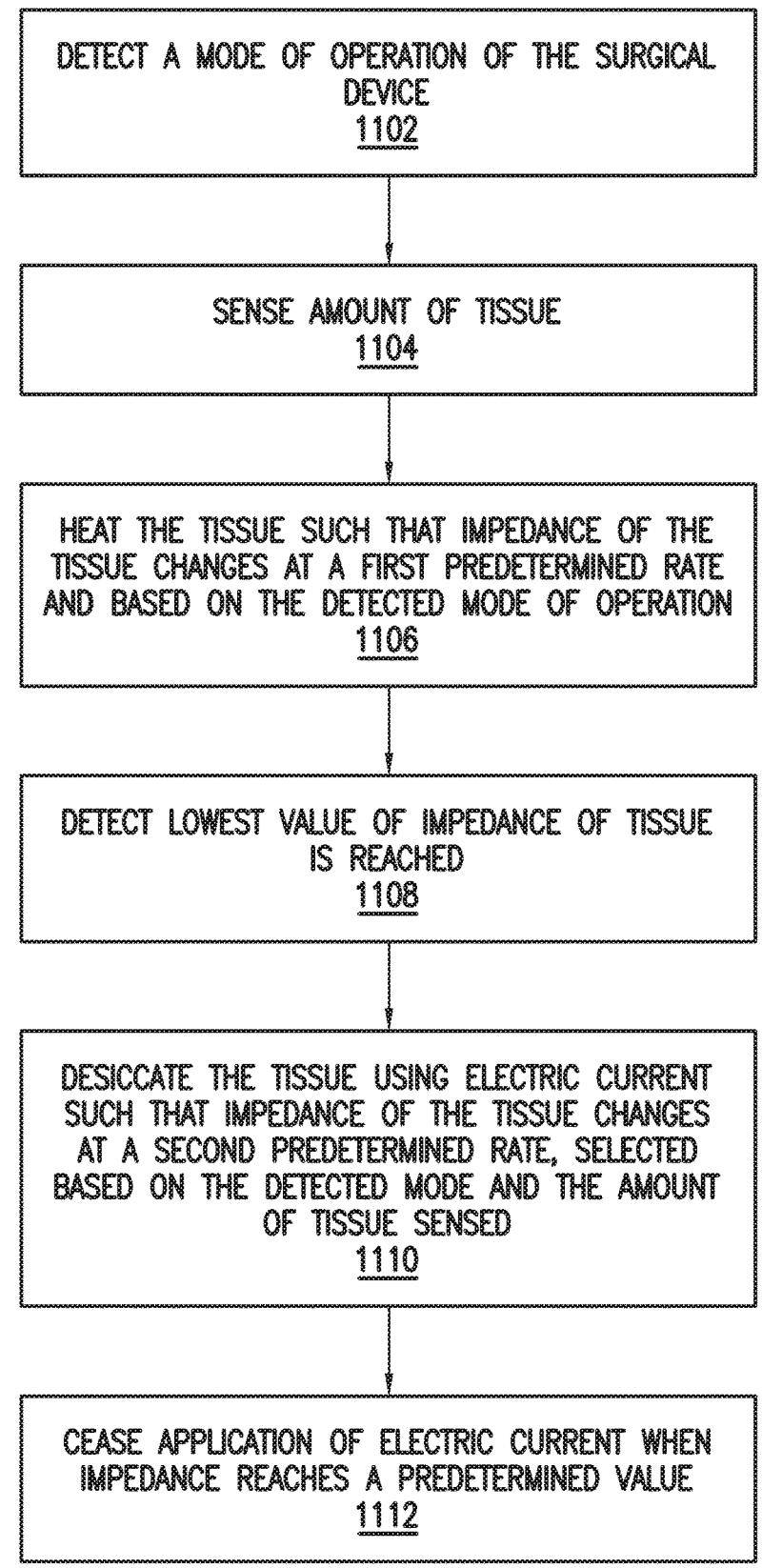
FIG. 11 shows a method in accordance with at least some embodiments.

Turning now to FIG. 11, another example method is discussed in accordance with at least some embodiments. The method generates a seal in a tissue that is held between jaws of a surgical device based on a mode of operation selected as well as an amount of tissue sensed by the surgical device. In various embodiments, some of the blocks shown in FIG. 11 may be performed concurrently, in a different order than shown, or omitted. Additional method elements may be performed as desired.

Initially, the vessel sealing system may detect of mode of operation of the surgical device (block 1102). As discussed previously, the mode of operation may optimize various aspects of the seal cycle as well as the generated seal. Next an amount of tissue present between jaws is sensed (step 1104). This may occur during the sensing phase of the seal cycle. Next, the surgical device may heat tissue held between jaws of the device such that impedance of the tissue changes at a first predetermined rate and based on the detected mode of operation (step 1106). In various embodiments, this might occur during the heating phase of the seal cycle. An amount of power applied during step 1106 may be limited based on the detected mode of operation. Additionally, a change of impedance of the tissue over time may be different depending on the detected mode of operation.

Next the vessel sealing system may detect that a lowest value of impedance of the tissue was reached (step 1108). At this juncture, the vessel sealing system may change control systems in preparation of beginning the next phase in the seal system. At this step, an adjustment as discussed above, may be used to determine that a lowest value of impedance of tissue was reached. Next the desiccating phase begins (step 1110). At step 1110, the jaws may desiccate the tissue using electric current such that impedance of the tissue changes at a second predetermined rate, selected based on the detected mode and the amount of tissue sensed. For example, a change of impedance of the tissue over time may be different depending on the detected mode of operation.

Finally, the application of electrical current is ceased when impedance reaches a predetermined value (step 1112). In various embodiments the ceasing of the application of electric current is determined by an algorithm implemented by way of the controller. At this point a seal is generated within the tissue held between the jaws.

From the description provided herein, those skilled in the art are readily able to combine software with appropriate general-purpose or special-purpose computer hardware to create a computer system and/or computer sub-components in accordance with the various embodiments and methods, for example, as discussed with regards to the vessel sealing system 100.

References to "one embodiment," "an embodiment," "some embodiments," "various embodiments," or the like indicate that a particular element or characteristic is included in at least one embodiment of the invention. Although the phrases may appear in various places, the phrases do not necessarily refer to the same embodiment or example.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

We claim:

1. A vessel sealing system comprising:
   forceps comprising a first jaw and an opposing second jaw, the first and second jaw configured to open and close relative to each other responsive to an actuator, and the first and second jaws electrically isolated from each other;
   a controller coupled to the forceps, the controller comprising:
   a processor;
   a memory coupled to the processor;
   an electrical generator operatively coupled to the processor, the electrical generator defines an active and a return terminal, the active terminal coupled to the first jaw, and the return terminal coupled to the second jaw, and the electrical generator configured to provide controllable electrical current to the first and second jaws;
   the memory storing a program that, when executed by the processor, causes the processor to seal a vessel residing within tissue between the first and second jaws by causing the processor to:
  sense an amount of the tissue held between the first and second jaws by varying a sense power delivered to the tissue from the electrical generator such that an electrical impedance of the tissue changes at a first predetermined rate of electrical impedance change that is constant, the sense power delivered indicative of the amount of the tissue held between the first and second jaws;
  select a second and a third predetermined rate of electrical impedance change based on the sense power delivered, the first, second, and third predetermined rates of electrical impedance change are all different from each other; and then
  heat the tissue using power from the electrical generator such that the electrical impedance of the tissue changes at the second predetermined rate of electrical impedance change; and then
  desiccate the tissue using the power from the electrical generator such that the electrical impedance of the tissue changes at the third predetermined rate of electrical impedance change; and then
  cease application of the power to the tissue when the electrical impedance of the tissue reaches a predetermined value.

2. The system of claim 1 wherein the step of causing the processor to sense the amount of the tissue held between the first and second jaws further comprises:
  calculating a mean power delivered to the tissue to achieve the first predetermined rate of electrical impedance change, the mean power delivered indicative of the amount of the tissue held between the first and second jaws.

3. The system of claim 2, wherein the first predetermined rate of electrical impedance change is about −50 Ohms/second.

4. The system of claim 1 wherein the first predetermined rate of electrical impedance change is about −50 Ohms/second for about 100 milliseconds.

5. The system of claim 1 wherein the second predetermined rate of electrical impedance change has a negative slope over the course of heating the tissue.

6. The system of claim 5 wherein the program further causes the processor to vary the power through the tissue to achieve the second predetermined rate of electrical impedance change until a lowest value of the electrical impedance multiplied by an adjustment factor is reached.

7. The system of claim 5 further comprising:
  a means for accepting an indication of a mode of operation of the system, the means for accepting operatively coupled to the processor, and
  the program on the memory, when executed by the processor, further causes the processor to:
    detect the mode of operation selected by an operator prior to the heating;
  heat the tissue at the second predetermined rate of electrical impedance change selected based on the amount of the tissue held between the first and second jaws and the mode of operation selected by the operator.

8. The system of claim 5 wherein the program further causes the processor to transition between heating and desiccation based on at least one selected from the group consisting of: at a lowest value of the electrical impedance of the tissue; after a rate of change of the electrical impedance transitions from negative to positive; and after the lowest value of the electrical impedance of the tissue is reached and surpassed by a predetermined amount.

9. The system of claim 1 wherein when the processor desiccates the tissue, the program causes the processor to vary the power through the tissue such that the third predetermined rate of electrical impedance change has a positive slope over the course of the desiccation.

10. The system of claim 9 further comprising:
  a means for accepting an indication of a mode of operation of the system, the means for accepting operatively coupled to the processor; and
  the program on the memory, when executed by the processor, further causes the processor to:
    detect the mode of operation selected by an operator prior to the desiccating;
    desiccate the tissue at the third predetermined rate of electrical impedance change selected based on the amount of the tissue and the mode of operation selected by the operator.

11. The system of claim 1: wherein when the processor desiccates the tissue, the program causes the processor to vary the power through the tissue such that the third predetermined rate of electrical impedance change has a positive slope over the course of the desiccation; and then the program further causes the processor to desiccate the tissue using the power such that the electrical impedance of the tissue changes at a fourth predetermined rate of electrical impedance change having a positive slope different than the slope of the third predetermined rate of electrical impedance change.

12. The system of claim 1 wherein when the processor desiccates the tissue, the program further causes the processor to vary the power through the tissue such that the third predetermined rate of electrical impedance change is defined by a set point electrical impedance as a function of time, where the set point electrical impedance as a function of time has the second predetermined rate of electrical impedance change, wherein the second predetermined rate of electrical impedance change comprises a predetermined path.

13. The system of claim 1 wherein when the processor desiccates the tissue, the program further causes the processor to vary the power through the tissue such that a first derivative of the electrical impedance as a function of time is the third predetermined rate of electrical impedance change.

14. A non-transitory computer-readable medium storing a program, that when executed by a processor, causes the processor to seal a vessel residing within tissue between a first and second jaw of a forceps by causing the processor to:
  sense an amount of the tissue held between the first and second jaws by varying an electrical current from an electrical generator through the tissue by way of the first and second jaws of the forceps, wherein varying the electrical current changes an electrical impedance of the tissue at a first predetermined rate of electrical impedance change that is constant;
  select a second and third predetermined rate of electrical impedance change based on the electrical current required to control the rate of change of electrical impedance of the tissue at the first predetermined rate of electrical impedance change, the first, second, and third predetermined rates of electrical impedance change are all different from each other; and then
  heat the tissue using the electrical current from the electrical generator such that the electrical impedance of the tissue changes at the second predetermined rate of electrical impedance change; and then desiccate the tissue using the electrical current from the electrical generator such that the electrical impedance of the tissue changes at the third predetermined rate of electrical impedance change different than the first predetermined rate of electrical impedance change; and then cease application of the electrical current to the tissue when the electrical impedance of the tissue reaches a predetermined value.

15. The non-transitory computer-readable medium of claim 14 wherein when the processor senses the amount of the tissue held between the first and second laws, the program causes the processor to:

calculate a mean electrical current delivered to the tissue during the determination of the amount of the tissue, the mean electrical current delivered indicative of the amount of the tissue held between the first and second jaws.

16. The non-transitory computer-readable medium of claim 15 wherein the first predetermined rate of electrical impedance change is about −50 Ohms/second.

17. The non-transitory computer-readable medium of claim 15 wherein the first predetermined rate of electrical impedance change is about −50 Ohms/second for about 100 milliseconds.

18. The non-transitory computer-readable medium of claim 14 wherein when the processor heats the tissue, the program causes the processor to vary the electrical current through the tissue such that the second predetermined rate of impedance change has a negative slope over a course of the heating.

19. The non-transitory computer-readable medium of claim 18 wherein the program, when executed by the processor, further causes the processor to vary the electrical current to achieve the second predetermined rate of electrical impedance change until a lowest value of the electrical impedance multiplied by an adjustment factor is reached.

20. The non-transitory computer-readable medium of claim 18 wherein the program, when executed by the processor, further causes the processor to:

detect a mode of operation of the forceps prior to the heating;

heat the tissue at the second predetermined rate of electrical impedance change selected based on the amount of the tissue held between the first and second jaws and the detected mode of operation.

21. The non-transitory computer-readable medium of claim 18 wherein the program, when executed by the processor, further causes the processor to transition between heating the tissue and desiccating the tissue based on at least one selected from the group consisting of: at a lowest value of the electrical impedance of the tissue; after the rate of change of electrical impedance transitions from negative to positive; and after the lowest value of the electrical impedance of the tissue is reached and surpassed by a predetermined amount.

22. The non-transitory computer-readable medium of claim 14 wherein the third predetermined rate of electrical impedance change has a positive slope over a course of the desiccation.

23. The non-transitory computer-readable medium of claim 22 wherein the program, when executed by the processor, further causes the processor to:

detect a mode of operation of the forceps prior to the desiccating;

desiccate the tissue at the third predetermined rate of electrical impedance change selected based on the amount of the tissue and the detected mode of operation.

24. The non-transitory computer-readable medium of claim 14 wherein when the processor desiccates the tissue, the program causes the processor to vary the electrical current through the tissue such that the third predetermined rate of electrical impedance change has a positive slope over a course of the desiccation; and then the program further causes the processor to desiccate the tissue using the electrical current such that the electrical impedance of the tissue changes at a fourth predetermined rate of electrical impedance change having a positive slope different than the slope of the third predetermined rate of electrical impedance change.

* * * * *